United States Patent
Essler

(10) Patent No.: US 9,486,547 B2
(45) Date of Patent: Nov. 8, 2016

(54) RADIOLABELLED ANTIBODY AND USES THEREOF

(71) Applicant: MorphoSys AG, Martinsried/Planegg (DE)

(72) Inventor: Markus Essler, Munich (DE)

(73) Assignee: MORPHOSYS AG, Martinsried/Planegg (DE)

( * ) Notice: Subject to any disclaimer, the term of this patent is extended or adjusted under 35 U.S.C. 154(b) by 0 days.

(21) Appl. No.: 14/438,882

(22) PCT Filed: Nov. 4, 2013

(86) PCT No.: PCT/EP2013/072944
§ 371 (c)(1),
(2) Date: Apr. 28, 2015

(87) PCT Pub. No.: WO2014/068114
PCT Pub. Date: May 8, 2014

(65) Prior Publication Data
US 2015/0283275 A1 Oct. 8, 2015

Related U.S. Application Data

(60) Provisional application No. 61/722,256, filed on Nov. 5, 2012.

(51) Int. Cl.
*A61K 39/395* (2006.01)
*A61K 51/10* (2006.01)
*C07K 16/40* (2006.01)

(52) U.S. Cl.
CPC ....... *A61K 51/1093* (2013.01); *A61K 51/1018* (2013.01); *C07K 16/40* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2002/0164788 A1  11/2002  Ellis

FOREIGN PATENT DOCUMENTS

| WO | 9962526 | 12/1999 |
|---|---|---|
| WO | 0206347 | 1/2002 |
| WO | 2005103083 | 11/2005 |
| WO | 2006099875 | 9/2006 |
| WO | 2006125640 | 11/2006 |
| WO | 2007042309 | 4/2007 |
| WO | 2008047242 | 4/2008 |
| WO | 2012041800 | 4/2012 |

OTHER PUBLICATIONS

PCT/EP2013/072944 International Search Report dated on Jan. 24, 2014.
U.S. Appl. No. 10/588,568, filed Nov. 11, 2010, Tesar.
U.S. Appl. No. 11/920,830, filed May 14, 2009, Tesar.
U.S. Appl. No. 12/089,806, filed Oct. 8, 2009, Tesar.
U.S. Appl. No. 11/886,932, filed Jun. 11, 2009, De Weers.
U.S. Appl. No. 12/441,466, filed Dec. 10, 2009, Park.

*Primary Examiner* — Sheela J Huff
(74) *Attorney, Agent, or Firm* — Licata & Tyrrell P.C.

(57) ABSTRACT

The present disclosure describes a radioconjugate of an anti-CD38 antibody and a radionuclide, e.g., $Bi^{213}$.

16 Claims, 16 Drawing Sheets

Figure 1

The amino acid sequence of the MOR202 Variable Heavy Domain is:

QVQLVESGGGLVQPGGSLRLSCAASGFTFSSYYMNWVRQAPGKGLEWVSGISGDPSNTYYADSVKGRFTISRDNSKNTLYLQMNSLRAEDTAVYYCARDLPLVYTGFAYWGQGTLVTVSS (SEQ ID NO: 10)

The amino acid sequence of the MOR202 Variable Light Domain is:

DIELTQPPSVSVAPGQTARISCSGDNLRHYYVYWYQQKPGQAPVLVIYGDSKRPSGIPERFSGSNSGNTATLTISGTQAEDEADYYCQTYTGGASLVFGGGTKLTVLGQ (SEQ ID NO: 11)

The amino acid sequence of the MOR202 HCDR1 as defined by an internal nomenclature is: GFTFSSYYMN (SEQ ID NO: 1)

The amino acid sequence of the MOR202 HCDR1 as defined by Kabat is: SYYMN (SEQ ID NO: 14)

The amino acid sequence of the MOR202 HCDR2 as defined by Kabat is: GISGDPSNTYYADSVKG (SEQ ID NO: 2)

The amino acid sequence of the MOR202 HCDR3 as defined by Kabat is: DLPLVYTGFAY (SEQ ID NO: 3)

The amino acid sequence of the MOR202 LCDR1 as defined by Kabat is: SGDNLRHYYVY (SEQ ID NO: 4)

The amino acid sequence of the MOR202 LCDR2 as defined by Kabat is: GDSKRPS (SEQ ID NO: 5)

The amino acid sequence of the MOR202 LCDR3 as defined by Kabat is: QTYTGGASL (SEQ ID NO:6)

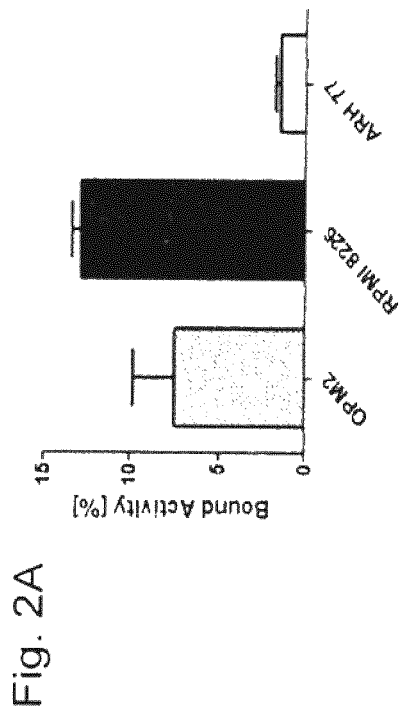
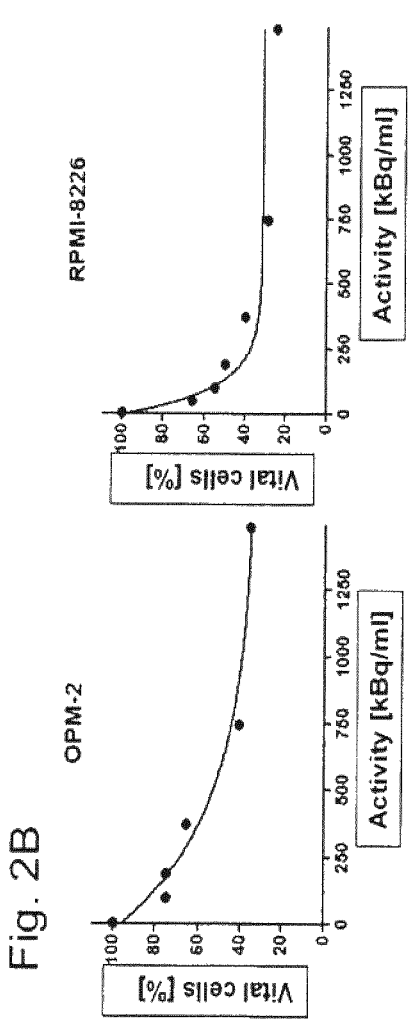
Fig. 2A
Fig. 2B

Time after treatment with $^{213}$Bi-anti-CD38-MAb (h)

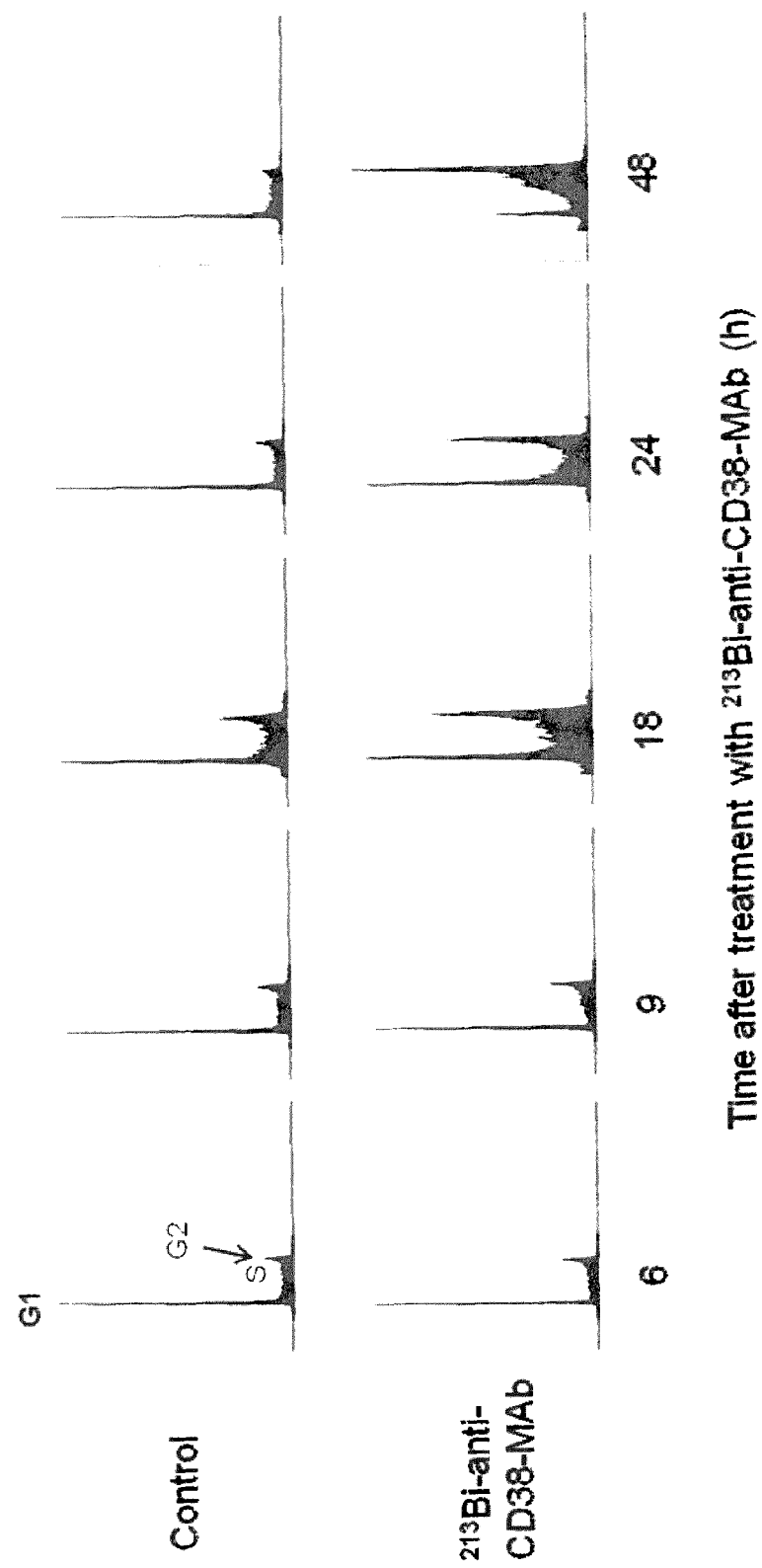

SEQUENCE LISTING

```
<160> NUMBER OF SEQ ID NOS: 14

<210> SEQ ID NO 1
<211> LENGTH: 10
<212> TYPE: PRT
<213> ORGANISM: Unknown
<220> FEATURE:
<223> OTHER INFORMATION: HCDR1 region of antibody specific for CD38

<400> SEQUENCE: 1

Gly Phe Thr Phe Ser Ser Tyr Tyr Met Asn
1               5                   10

<210> SEQ ID NO 2
<211> LENGTH: 17
<212> TYPE: PRT
<213> ORGANISM: Unknown
<220> FEATURE:
<223> OTHER INFORMATION: HCDR2 region of antibody specific for CD38

<400> SEQUENCE: 2

Gly Ile Ser Gly Asp Pro Ser Asn Thr Tyr Tyr Ala Asp Ser Val Lys
1               5                   10                  15

Gly

<210> SEQ ID NO 3
<211> LENGTH: 11
<212> TYPE: PRT
<213> ORGANISM: Unknown
<220> FEATURE:
<223> OTHER INFORMATION: HCDR3 region of antibody specific for CD38
```

```
<400> SEQUENCE: 3

Asp Leu Pro Leu Val Tyr Thr Gly Phe Ala Tyr
  1               5                  10

<210> SEQ ID NO 4
<211> LENGTH: 11
<212> TYPE: PRT
<213> ORGANISM: Unknown
<220> FEATURE:
<223> OTHER INFORMATION: LCDR1 region of antibody specific for CD38

<400> SEQUENCE: 4

Ser Gly Asp Asn Leu Arg His Tyr Tyr Val Tyr
  1               5                  10

<210> SEQ ID NO 5
<211> LENGTH: 7
<212> TYPE: PRT
<213> ORGANISM: Unknown
<220> FEATURE:
<223> OTHER INFORMATION: LCDR2 region of antibody specific for CD38

<400> SEQUENCE: 5

Gly Asp Ser Lys Arg Pro Ser
  1               5

<210> SEQ ID NO 6
<211> LENGTH: 9
<212> TYPE: PRT
<213> ORGANISM: Unknown
<220> FEATURE:
<223> OTHER INFORMATION: LCDR3 region of antibody specific for CD38

<400> SEQUENCE: 6

Gln Thr Tyr Thr Gly Gly Ala Ser Leu
  1               5

<210> SEQ ID NO 7
<211> LENGTH: 300
<212> TYPE: PRT
<213> ORGANISM: Homo sapiens
<220> FEATURE:
<223> OTHER INFORMATION: Human CD38 sequence

<400> SEQUENCE: 7

Met Ala Asn Cys Glu Phe Ser Pro Val Ser Gly Asp Lys Pro Cys Cys
  1               5                  10                  15

Arg Leu Ser Arg Arg Ala Gln Leu Cys Leu Gly Val Ser Ile Leu Val
                 20                  25                  30

Leu Ile Leu Val Val Val Leu Ala Val Val Pro Arg Trp Arg Gln
             35                  40                  45

Gln Trp Ser Gly Pro Gly Thr Thr Lys Arg Phe Pro Glu Thr Val Leu
         50                  55                  60

Ala Arg Cys Val Lys Tyr Thr Glu Ile His Pro Glu Met Arg His Val
 65                  70                  75                  80

Asp Cys Gln Ser Val Trp Asp Ala Phe Lys Gly Ala Phe Ile Ser Lys
                 85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
            115                 120                 125
```

```
Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
                180                 185                 190

Ser Arg Arg Phe Ala Glu Ala Ala Cys Asp Val Val His Val Met Leu
            195                 200                 205

Asn Gly Ser Arg Ser Lys Ile Phe Asp Lys Asn Ser Thr Phe Gly Ser
210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
                260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
290                 295                 300

<210> SEQ ID NO 8

<400> SEQUENCE: 8

000

<210> SEQ ID NO 9

<400> SEQUENCE: 9

000

<210> SEQ ID NO 10
<211> LENGTH: 120
<212> TYPE: PRT
<213> ORGANISM: Unknown
<220> FEATURE:
<223> OTHER INFORMATION: variable heavy chain of antibody specific for
      CD38

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asp Pro Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110
```

Gly Thr Leu Val Thr Val Ser Ser
          115                 120

<210> SEQ ID NO 11
<211> LENGTH: 109
<212> TYPE: PRT
<213> ORGANISM: Unknown
<220> FEATURE:
<223> OTHER INFORMATION: variable heavy chain of antibody specific for
      CD38

<400> SEQUENCE: 11

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Arg His Tyr Tyr Val
            20                  25                  30

Tyr Trp Tyr Gln Gln Lys Pro Gly Gln Ala Pro Val Leu Val Ile Tyr
        35                  40                  45

Gly Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105

<210> SEQ ID NO 12
<211> LENGTH: 360
<212> TYPE: DNA
<213> ORGANISM: Artificial Sequence
<220> FEATURE:
<223> OTHER INFORMATION: DNA sequence encoding the MOR202 Variable Heavy
      Domain

<400> SEQUENCE: 12
caggtgcaat tggtggaaag cggcggcggc ctggtgcaac cgggcggcag cctgcgtctg      60
agctgcgcgg cctccggatt tacctttttct tcttattata tgaattgggt gcgccaagcc   120
cctgggaagg gtctcgagtg ggtgagcggt atctctggtg atcctagcaa taccattat    180 gcggatagcg tgaaaggccg ttttaccatt tcacgtgata attcgaaaaa cacccctgtat   240 ctgcaaatga acagcctgcg tgcggaagat acggccgtgt attattgcgc gcgtgatctt   300
cctcttgttt atactggttt tgcttattgg ggccaaggca ccctggtgac ggttagctca    360

<210> SEQ ID NO 13
<211> LENGTH: 327
<212> TYPE: DNA
<213> ORGANISM: Artificial Sequence
<220> FEATURE:
<223> OTHER INFORMATION: DNA sequence encoding the MOR202 Variable Light
      Domain

<400> SEQUENCE: 13
gatatcgaac tgacccagcc gccttcagtg agcgttgcac caggtcagac cgcgcgtatc      60
tcgtgtagcg gcgataatct tcgtcattat tatgtttatt ggtaccagca gaaacccggg    120
caggcgccag ttcttgtgat ttatggtgat tctaagcgtc cctcaggcat cccggaacgc    180
tttagcggat ccaacagcgg caacaccgcg accctgacca ttagcggcac tcaggcggaa    240
gacgaagcgg attattattg ccagacttat actggtggtg cttctcttgt gtttggcggc    300

```
ggcacgaagt taaccgttct tggccag                                              327
```

<210> SEQ ID NO 14
<211> LENGTH: 5
<212> TYPE: PRT
<213> ORGANISM: Unknown
<220> FEATURE:
<223> OTHER INFORMATION: HCDR1 region of antibody specific for CD38

<400> SEQUENCE: 14

Ser Tyr Tyr Met Asn
 1               5

RADIOLABELLED ANTIBODY AND USES THEREOF

This application claims benefit, under 35 U.S.C. §119(e), of U.S. patent application No. 61/722,256, filed on Nov. 5, 2012, which is hereby incorporated by reference in its entirety.

1. FIELD

The present disclosure relates to an anti-CD38 antibody radiolabelled with an α-particle emitting isotope, e.g., $^{213}$Bi (also known as "radioconjugate"). Such a radiolabelled antibody is useful in the treatment of cancers, such as, multiple myeloma and/or non-Hodgkin's lymphoma.

2. BACKGROUND

Multiple myeloma is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system.

Approximately 1% of all cancers, and slightly more than 10% of all hematologic malignancies, can be attributed to multiple myeloma (MM). The incidence of MM increases in the aging population, with the median age at time of diagnosis being about 61 years. The currently available therapies for multiple myeloma include chemotherapy, stem cell transplantation, Thalomid® (thalidomide), Velcade® (bortezomib), Aredia® (pamidronate), and Zometa® (zoledronic acid). The current treatment protocols, which include a combination of chemotherapeutic agents such as vincristine, BCNU, melphalan, cyclophosphamide, adriamycin, and prednisone or dexamethasone, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Yet overall survival has only been slightly prolonged, and no evidence for a cure has been obtained. Ultimately, MM patients often relapse, even under maintenance therapy with interferon-alpha (IFN-α) alone or in combination with steroids.

Non-Hodgkin's lymphoma is a broad classification of lymphomas, which are cancers originating from the lymphatic system when lymphocytes (B-cells or T-cells) become malignant and proliferate uncontrollably to form a tumor mass. In total NHL encompasses around 30 different subtypes of lymphoma, including Diffuse large B-cell lymphoma (DLBCL) and follicular lymphoma (FL). The incidence of NHL will reach over 140,000 in the major markets by 2019. The available treatment options include Rituxan/MabThera, combinations thereof, such as, R-CHOP (rituximab, cyclophosphamide, doxorubicin, vincristine and prednisone), R-CVP (Rituxan, cyclophosphamide, vincristine and prednisone), and chemotherapy. In addition, following remission or after relapse, hematopoietic stem cell transplantation may be considered. Despite the current treatment options, however, the survival rates within high risk groups of aggressive NHL can be as low as 30% over 5 years. Therefore, there remains a high unmet need for effective treatments and combination treatments.

CD38 is an example of an antigen expressed on such malignant plasma cells, and other lymphocytes. Functions ascribed to CD38 include both receptor mediation in adhesion and signaling events and (ecto-) enzymatic activity. As an ectoenzyme, CD38 uses NAD+ as substrate for the formation of cyclic ADP-ribose (cADPR) and ADPR, but also of nicotinamide and nicotinic acid-adenine dinucleotide phosphate (NAADP). cADPR and NAADP have been shown to act as second messengers for Ca2+ mobilization. By converting NAD+ to cADPR, CD38 regulates the extracellular NAD+ concentration and hence cell survival by modulation of NAD-induced cell death (NCID). In addition to signaling via Ca2+, CD38 signaling occurs via cross-talk with antigen-receptor complexes on T and B cells or other types of receptor complexes, e.g. MHC molecules, and is in this way involved in several cellular responses, but also in switching and secretion of IgG.

Antibodies specific for CD38 are described in WO1999/62526 (Mayo Foundation); WO200206347 (Crucell Holland); US2002164788 (Jonathan Ellis) which is incorporated by reference in its entirety; WO2005/103083 (MorphoSys AG), U.S. Ser. No. 10/588,568, which is incorporated by reference in its entirety, WO2006/125640 (MorphoSys AG), U.S. Ser. No. 11/920,830, which is incorporated by reference in its entirety, and WO2007/042309 (MorphoSys AG), U.S. Ser. No. 12/089,806, which is incorporated by reference in its entirety; WO2006099875 (Genmab), U.S. Ser. No. 11/886,932, which is incorporated by reference in its entirety; and WO08/047242 (Sanofi-Aventis), U.S. Ser. No. 12/441,466, which is incorporated by reference in its entirety.

Antibodies labeled with radionuclides may also be used therapeutically. Their use is based on the preferential targeting of the radionuclides to certain cells and tissues but not others. For example, high energy radionuclides may be targeted to tissue where the high energy has a cell damaging or cytotoxic effect on the targeted cells.

It is clear that in spite of the recent progress in the discovery and development of anti-cancer agents, many forms of cancer involving CD38-expressing tumors still have a poor prognosis. Thus, there is a need for improved methods for treating such forms of cancer.

3. SUMMARY

In one aspect, the present disclosure relates to an anti-CD38 antibody radiolabelled with an α-particle emitting isotope, e.g., $^{213}$Bi. Such a radiolabelled antibody (also referred to herein as a "radioconjugate") is useful in the treatment of cancers, such as, multiple myeloma and/or non-Hodgkin's lymphoma.

In vitro and in vivo models are considered predictive of how a certain compound or combination of compounds would behave in humans. Here, the radioconjugate of an antibody specific for CD38 and $^{213}$Bi was tested in human multiple myeloma cell lines and a mouse model and strong effect was identified.

An aspect of the present disclosure relates to a radioconjugate comprising an antibody specific for CD38 comprises an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and a radionuclide, for example, an α-particle emitting radionuclide, e.g. $^{213}$Bi. In certain aspects, the radioconjugate is used for the treatment of multiple myeloma and/or non-Hodgkin's lymphoma.

In a particular embodiment, the HCDR1 region of such a radioconjugate comprises SYYMN (SEQ ID NO: 14). In another particular embodiment, the radionuclide comprises an In α-particle emitting isotope. In yet another particular embodiment, such a radioconjugate comprises, for example, iodine-131, yttrium-90, lutetium-177, copper-67, astatine-211, bismuth-212, bismuth-213, and actinium-225. In a specific embodiment, the radionuclide is bismuth-213.

In a specific embodiment, the radioconjugate can comprise an antibody region that comprises a variable heavy chain of the sequence: QVQLVESGGGLVQPGGSLRLSCAASGFTFSSYYM NWVRQAPGKGLEWVSGISGDPSNTYYADSVKGR FTISRDNSKNTLYLQMNSLRAEDTAVYYCARDLPLVYTGFAYWGQGTLVTVSS (SEQ ID NO: 10), and a variable light chain of the sequence: DIELTQPPSVSVAPGQTARISCSGDNLRHYYVYW YQQKPGQAPVLVIYGDSKRPSGIPERFSGSNSG NTATLTISGTQAEDEADYYCQTYTGGASLVFGGGTKLTVLGQ (SEQ ID NO: 11).

In certain embodiments, the radioconjugate can comprise an antibody that comprises an Fc region, for example, an IgG1 Fc region. In certain additional embodiments, the radioconjugate can comprise a modified Fc region, for example, a modified Fc region wherein the modification enhances ADCC and/or CDC activity.

In another aspect, presented herein are methods comprising administration of a radioconjugate described herein. For example, in one embodiment, presented herein is a method of treating multiple myeloma in an individual in need thereof, comprising administration of a radioconjugate described herein. In a particular embodiment, such a method can comprise administering a radioconjugate described herein in which the radioconjugate comprises an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and $^{213}$Bi.

In a specific embodiment, such a method can comprise administering a radioconjugate wherein the HCDR1 region of the radioconjugate comprises SYYMN (SEQ ID NO: 14). In another specific embodiment, such a method can comprise administering a radioconjugate that comprise an antibody region comprising a variable heavy chain of the sequence QVQLVESGGGLVQPGGSLRLSCAASGFTFSSYY MNWVRQAPGKGLEWVSGISGDPSNTYYADSV KGRFTISRDNSKNTLYLQMNSLRAEDTAVYYCARDLPLVYTGFAYWGQGTLVTVSS (SEQ ID NO: 10) and a variable light chain of the sequence DIELTQPPSVSVAPGQTARISCSGDNLRHYYVYW YQQKPGQAPVLVIYGDSKRPSGIPERFSGSNSGN TATLTISGTQAEDEADYYCQTYTGGASLVFGGGTKLTVLGQ (SEQ ID NO: 11).

In yet another embodiment, presented herein is a method of treating non-hodgkin's lymphoma in an individual in need thereof, comprising administration of a radioconjugate according to any of the preceding claims. In a particular embodiment, such a method can comprise administering a radioconjugate that comprises an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and $^{213}$Bi.

In another specific embodiment, such a method can comprise administering a radioconjugate wherein the HCDR1 region of the radioconjugate comprises SYYMN (SEQ ID NO: 14). In yet another specific embodiment, such a method can comprise administering a radioconjugate that comprises an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and $^{213}$Bi.

4. DESCRIPTION OF DRAWINGS

FIG. 1 shows the amino acid sequence of MOR202.

FIG. 2A-2B shows the binding of $^{213}$Bi-anti-CD38-MAb to myeloma cell lines and the correlation of $^{213}$Bi-anti-CD38-MAb binding and cytotoxicity. FIG. 2A: Percentages of $^{213}$Bi-anti-CD38-MAb binding to the multiple myeloma cell lines OPM2, RPMI8226 and ARH77 as quantified by bound $^{213}$Bi activity in the cell pellet. FIG. 2B: Assessment of cytotoxicity of $^{213}$Bi-anti-CD38-MAb upon OPM2, RPMI and ARH77 myeloma cells as quantified by the CellTiter96® cell proliferation assay 48 h after initiation of treatment.

Figure 6:
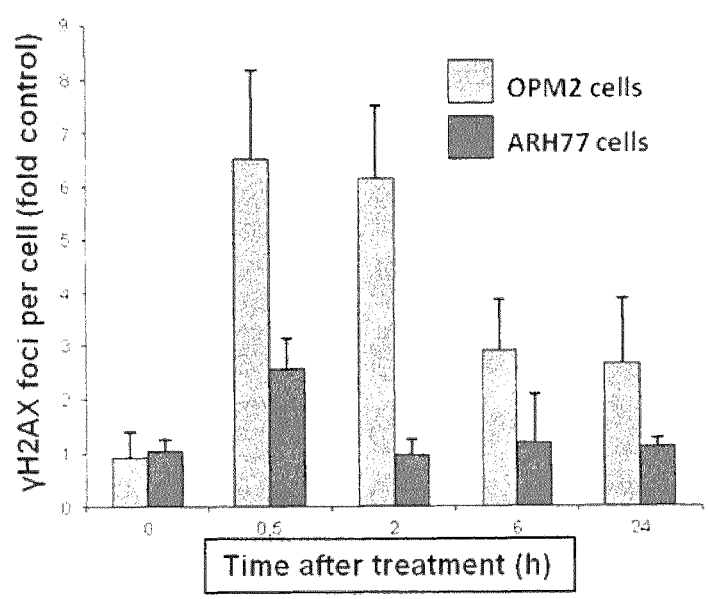

FIG. 6. Quantification of $^{213}$Bi-anti-CD38-MAb induced DNA double strand breaks. OPM2 or ARH77 multiple myeloma cells were treated with $^{213}$Bi-anti-CD38-MAb (1.48 MBq/ml) for 3 h at 4° C. to prevent DNA repair. Subsequently, cells were washed with PBS and incubated at 37° C. in fresh medium. At the indicated time points cells were stained for γH2AX and the signals (foci per cell) were quantified using Definiens© software.

Figure 7A:
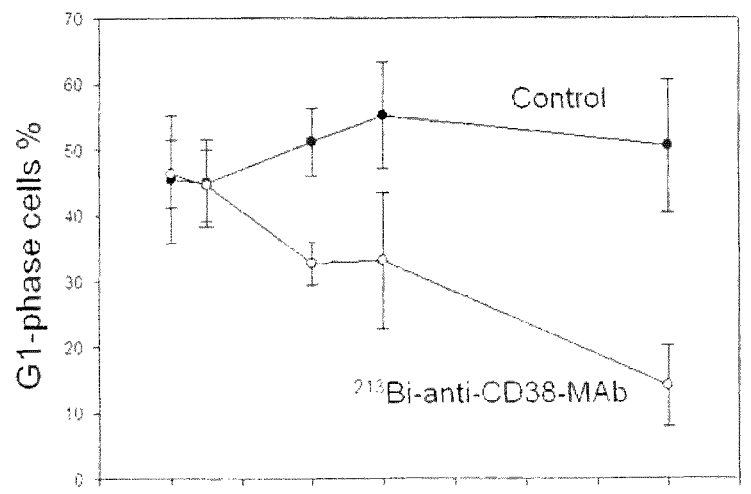
Figure 7B:
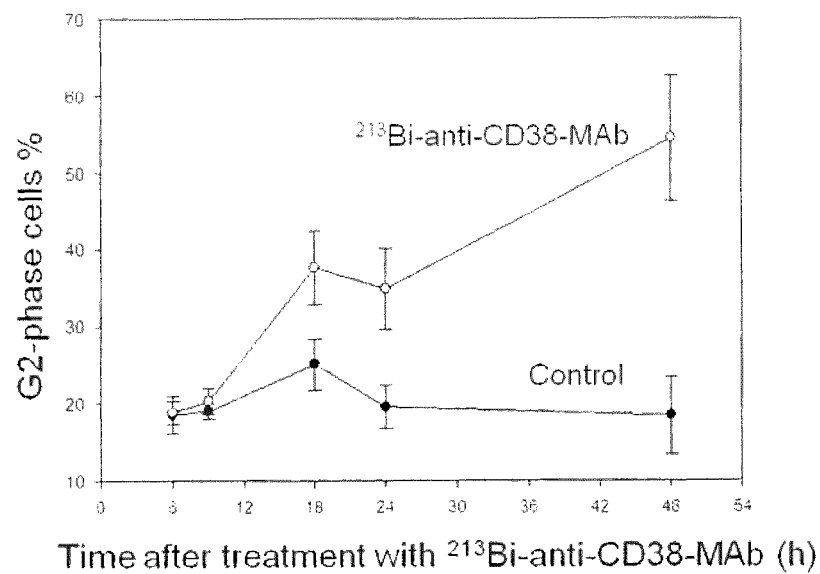

FIG. 7A-7C. $^{213}$Bi-anti-CD38-MAb induced cell cycle arrest. Percentages of OPM2 cells in the G1-phase (FIG. 7A) and the G2-phase (FIG. 7B) of the cell cycle were determined at the indicated time points after treatment with $^{213}$Bi-anti-CD38 immunoconjugates (1.48 MBq/ml, 3 h, 37° C.). Means of three independent experiments±SD are shown. In FIG. 7C, the corresponding histograms of one representative experiment are depicted.

FIG. 8A-8D. Signal mechanisms triggering $^{213}$Bi-anti-CD38-MAb induced cell cycle arrest and apoptosis. DNA content (FIG. 8A) and histone H3 phosphorylation (FIG. 8B) in OPM2 cells 120 h after treatment with $^{213}$Bi-anti-CD38-MAb (0.74 MBq/ml) or PBS (control) as determined by flow cytometry. Expression of major G2/M checkpoint activating and pro-apoptotic proteins (FIG. 8C) as well as caspase-3 activation and PARP cleavage (FIG. 8D) at different time points after incubation of OPM2 cells with $^{213}$Bi-anti-CD38-MAb (0.74 MBq/ml) as determined by immunoblotting.

Figure 9:
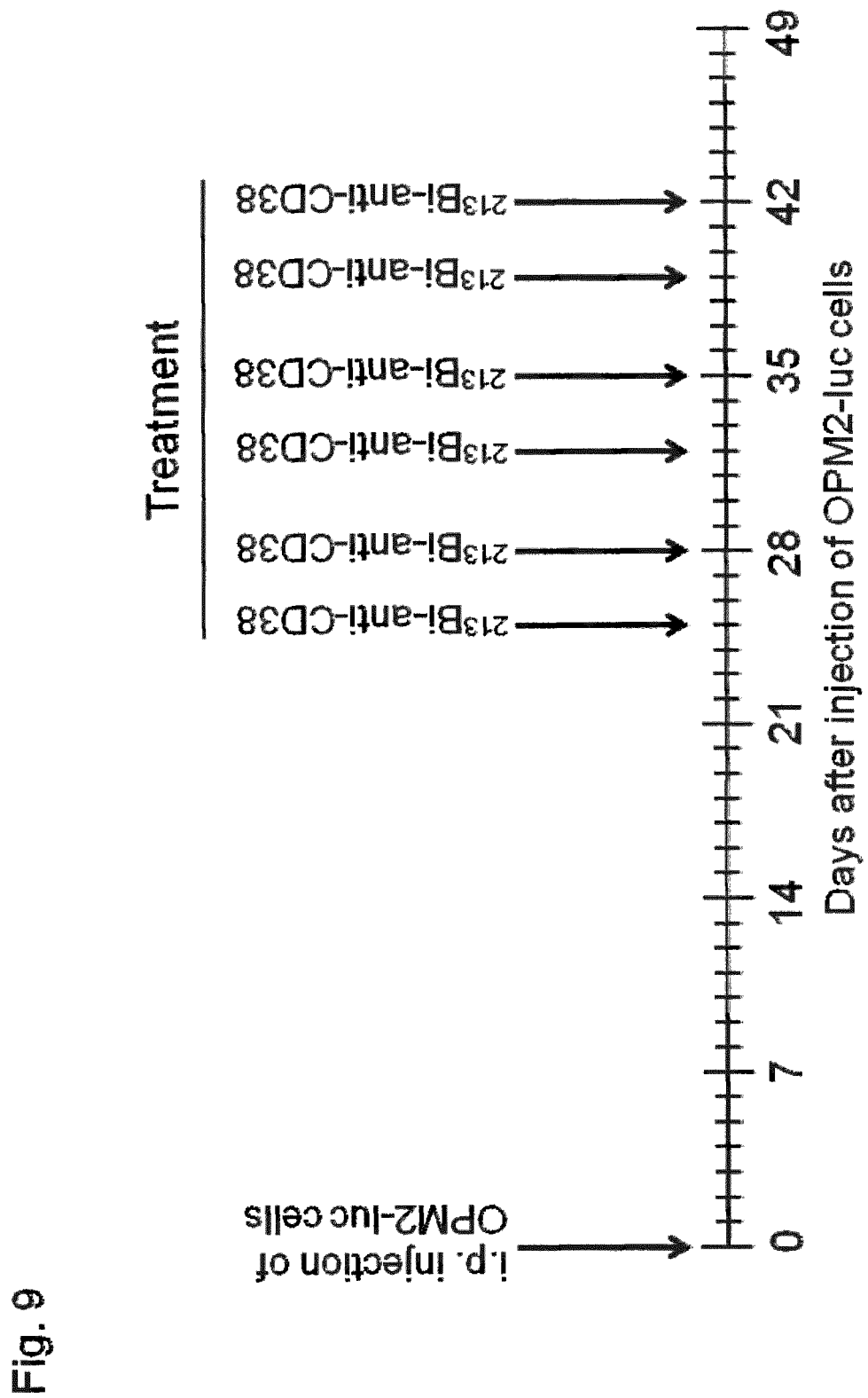

FIG. 9. Preclinical treatment study. Mice were treated six times with 1.85 MBq of $^{213}$Bi-anti-CD38-MAb, unspecific $^{213}$Bi-DTPA or PBS (control) between day 25 and 42 after inoculation of OPM2 multiple myeloma cells, as indicated.

Figure 10:
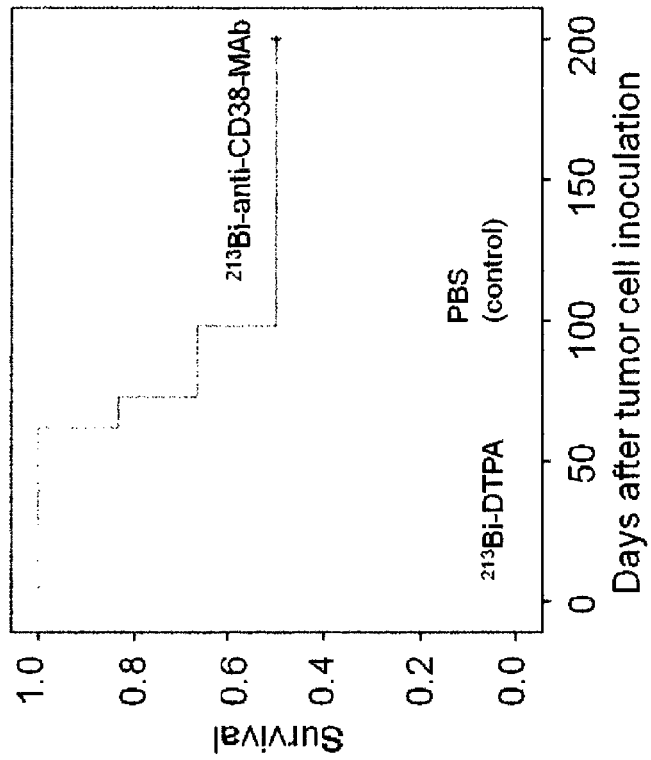

FIG. 10. Kaplan-Meyer plot showing the survival of mice after treatment with PBS (control), unspecific $^{213}$Bi-DTPA, and $^{213}$Bi-anti-CD38-MAb.

Figure 11:
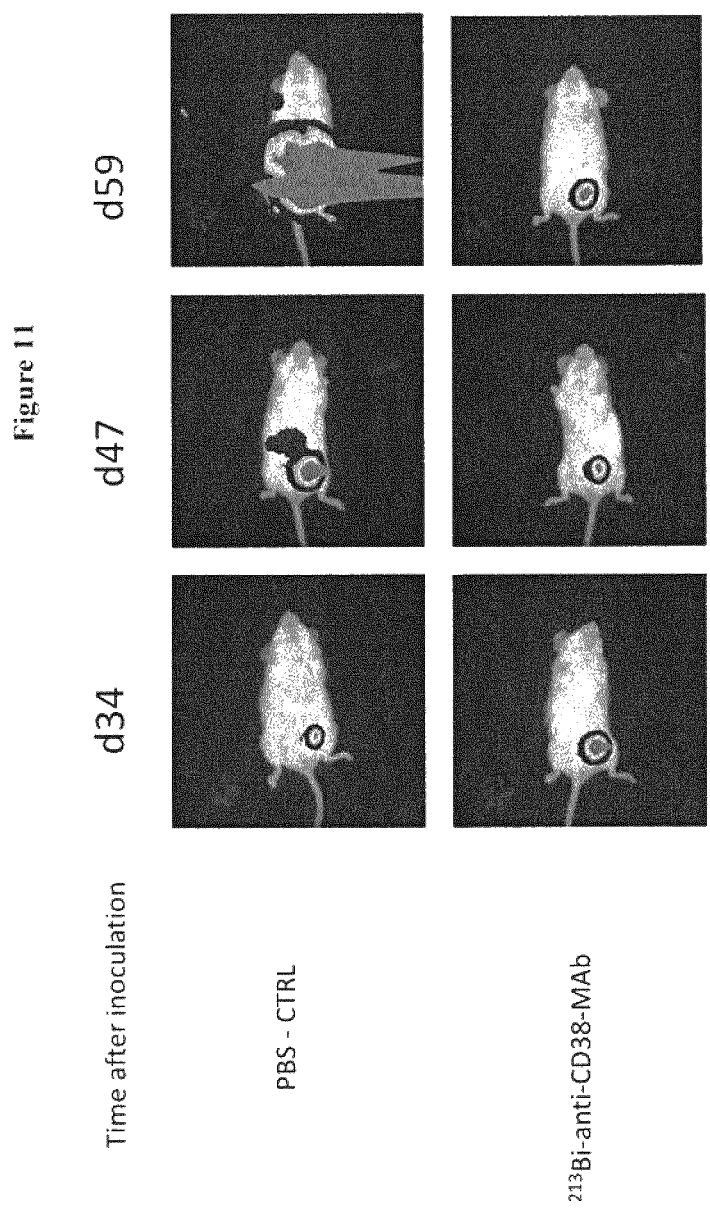

FIG. 11. Bioluminescence imaging of tumor development at days 34, 47, and 59 after tumor cell inoculation in control and $^{213}$Bi-anti-CD38-MAb treated animals.

Figure 12:
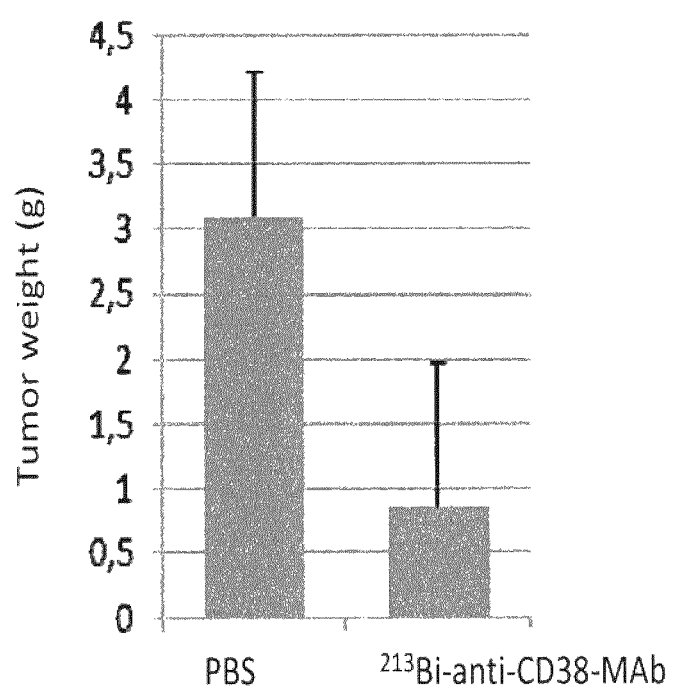

FIG. 12. Weights of tumor tissue two weeks after the final treatment cycle in mice treated with PBS (control) and $^{213}$Bi-anti-CD38-MAb.

Figure 13B:
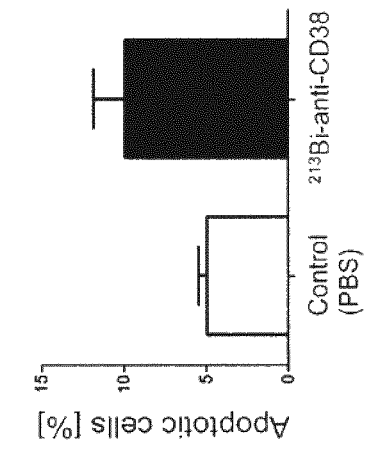
Figure 13A:
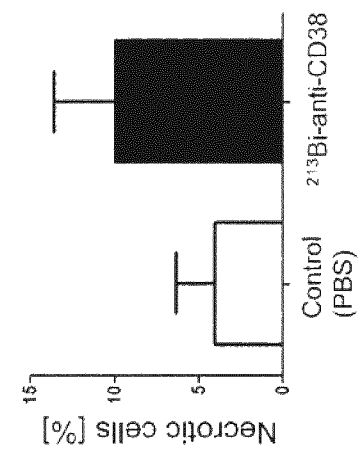
Figure 13C:
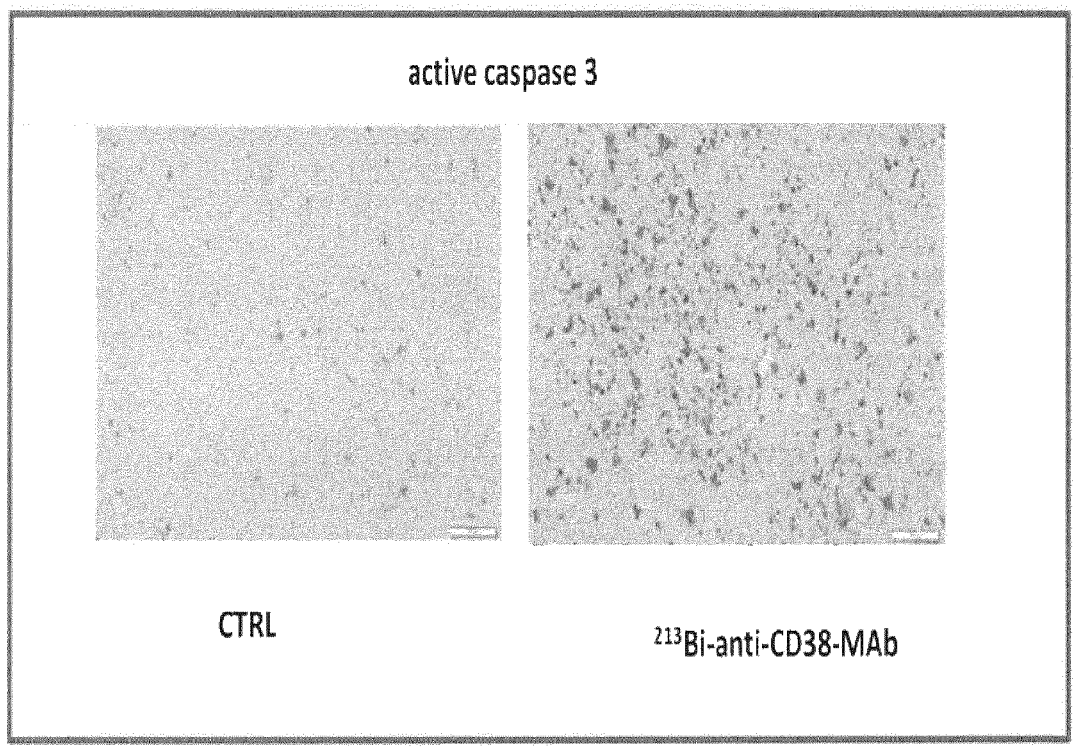

FIG. 13A-13C. Assessment of intratumoral apoptosis and necrosis. Two weeks after therapy intratumoral apoptosis and necrosis were determined on paraffin slices of tumor tissue. FIG. 13A: Immunohistochemical detection of apoptotic cells by staining of active caspase-3. FIG. 13B: quantification of apoptotic cells. FIG. 13C: necrotic cells on H&E stained tumor tissue sections using Definiens© TissueMap software.

5. DETAILED DESCRIPTION OF THE INVENTION

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions.

"VH" refers to the variable region of an immunoglobulin heavy chain of an antibody, or antibody fragment. "VL" refers to the variable region of the immunoglobulin light chain of an antibody, or antibody fragment.

The "CDRs" herein are defined by either Chothia et al., Kabat et al. or by an internal numbering convention. See Chothia C, Lesk A M. (1987) Canonical structures for the hypervariable regions of immunoglobulins. J Mol Biol., 196(4):901-17, which is incorporated by reference in its entirety. See Kabat E. A, Wu T. T., Perry H. M., Gottesman K. S. and Foeller C. (1991). Sequences of Proteins of Immunological Interest. 5th edit., NIH Publication no. 91-3242, US Dept. of Health and Human Services, Washington, D.C., which is incorporated by reference in its entirety.

The term "CD38" refers to the protein known as CD38, having the following synonyms: ADP-ribosyl cyclase 1, cADPr hydrolase 1, Cyclic ADP-ribose hydrolase 1, T10.

Human CD38 has the amino acid sequence of:

```
                                          (SEQ ID NO: 7)
MANCESPVSGDKPCCRLSRRAQLCLGVSILVLILVVVLAVVVPRWRQQW

SGPGTTKRFPETVLARCVKYTEIHPEMRHVDCQSVWDAFKGAFISKHPC

NITEEDYQPLMKLGTQTVPCNKILLWSRIKDLAHQFTQVQRDMFTLEDT

LLGYLADDLTWCGEFNTSKINYQSCPDWRKDCSNNPVSVFWKTVSRRFA

EAACDVVHVMLNGSRSKIFDKNSTFGSVEVHNLQPEKVQTLEAWVIHGG

REDSRDLCQDPTIKELESIISKRNIQFSCKNIYRPDKFLQCVKNPEDSS

CTSEI.
```

"MOR202" an anti-CD38 antibody whose amino acid sequence is provided in FIG. 1. "MOR202" and "MOR03087" are used as synonyms to describe the antibody shown in FIG. 1.

A representative DNA sequence encoding the MOR202 Variable Heavy Domain is:

```
                                          (SEQ ID NO: 12)
CAGGTGCAATTGGTGGAAAGCGGCGGCGGCCTGGTGCAACCGGGCGGCA

GCCTGCGTCTGAGCTGCGCGGCCTCCGGATTTACCTTTTCTTCTTATTA

TATGAATTGGGTGCGCCAAGCCCCTGGGAAGGGTCTCGAGTGGGTGAGC

GGTATCTCTGGTGATCCTAGCAATACCTATTATGCGGATAGCGTGAAAG

GCCGTTTTACCATTTCACGTGATAATTCGAAAAACACCCTGTATCTGCA

AATGAACAGCCTGCGTGCGGAAGATACGGCCGTGTATTATTGCGCGCGT

GATCTTCCTCTTGTTTATACTGGTTTTGCTTATTGGGGCCAAGGCACCC

TGGTGACGGTTAGCTCA
```

A representative DNA sequence encoding the MOR202 Variable Light Domain is:

```
                                          (SEQ ID NO: 13)
GATATCGAACTGACCCAGCCGCCTTCAGTGAGCGTTGCACCAGGTCAGA

CCGCGCGTATCTCGTGTAGCGGCGATAATCTTCGTCATTATTATGTTTA

TTGGTACCAGCAGAAACCCGGGCAGGCGCCAGTTCTTGTGATTTATGGT

GATTCTAAGCGTCCCTCAGGCATCCCGGAACGCTTTAGCGGATCCAACA

GCGGCAACACCGCGACCCTGACCATTAGCGGCACTCAGGCGGAAGACGA

AGCGGATTATTATTGCCAGACTTATACTGGTGGTGCTTCTCTTGTGTTT

GGCGGCGGCACGAAGTTAACCGTTCTTGGCCAG.
```

A "combination" means more than one item.

A "radioconjugate" is an antibody that is labeled with a radionuclide. A radioconjugate is considered a combination of an antibody and a radionuclide.

The terms "radionuclide" and "radioisotope" are used interchangeably to refer to atoms with an unstable nucleus, which is a nucleus characterized by excess energy which is available to be imparted either to a newly-created radiation particle within the nucleus, or else to an atomic electron. The radionuclide, in this process, undergoes radioactive decay. Radionuclides may occur naturally, but can also be artificially produced. Radionuclides vary based on their characteristics, which include half-life, energy emission characteristics, and type of decay. This allows one to select radionuclides that have the desired mixture of characteristics suitable for use diagnostically and/or therapeutically. For example, gamma emitters are generally used diagnostically and beta emitters are generally used therapeutically. However, some radionuclides are both gamma emitters and beta emitters, and thus, may be suitable for both uses by altering the amount of radioactivity used (the total and/or specific activity).

Radionuclides used to radiolabel include, but are not limited to, carbon-11, nitrogen-13, oxygen-15, fluorine-18, copper-67, gallium-67, gallium-68, krypton-81m, rubidium-82, technetium-99m, indium-11, iodine-123, iodine-124, iodine-125, iodine-131, xenon-133, thallium-201, zirconium-89, copper-64, yttrium-90, technetium-99m, iodine-123, iodine-124, and iodine-125, lutetium-177, At-211, lead-212, bismuth-212, bismuth-213, and actinium-225. These radionuclides, as well as their characteristics (e.g., half-life, emission, etc) are well known in the art, as are methods of making them and labeling proteins with them. Thus, one can select amongst available radionuclides to select the radionuclide with the appropriate combination of characteristics based on the particular application.

Radionuclides that can be used to damage cells, such as cancer cells, are high energy emitters. For example, a high energy radionuclide is selected and targeted to cancer cells. The high energy radionuclide preferably acts over a short range so that the cytotoxic effects are localized to the targeted cells. In this way, radiotherapy is delivered in a more localized fashion to decrease damage to non-cancerous cells. In certain embodiments, the suitable radionuclide is an alpha or beta emitting radionuclide.

In certain embodiments, the radionuclide suitable for use as a radioconjugate to damage cells is selected from the group consisting of iodine-131, yttrium-90, lutetium-177, copper-67, astatine-211, bismuth-212, bismuth-213, and actinium-225. In certain embodiments, the radionuclide is bismuth-213.

Bismuth is an element with symbol Bi and atomic number 83. The radioactive isotope, bismuth-213 can be produced by bombarding radium with bremsstrahlung photons from a linear particle accelerator. In 1997, an antibody conjugate with bismuth-213, which has a 45-minute half-life and decays with the emission of an alpha particle, was used to treat patients with leukemia. This isotope has also been tried in cancer treatment, for example, in the targeted alpha therapy (TAT) program.

The disclosure contemplates that antibody or antibody fragment may be labeled with a radionuclide using any available method and chemistry. Association or conjugation of the radionuclide may be directly or via a coupling agent or linker, e.g. a chelator.

A pharmaceutical composition includes an active agent, eg. an antibody for therapeutic use in humans. A pharmaceutical composition may include acceptable carriers or excipients.

"Administered" or "administration" includes but is not limited to delivery by an injectable form, such as, for example, an intravenous, intramuscular, intradermal or subcutaneous route or mucosal route, for example, as a nasal spray or aerosol for inhalation or as an ingestable solution, capsule or tablet.

A "therapeutically effective amount" of a compound or combination refers to an amount sufficient to cure, alleviate or partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

6. EMBODIMENTS

An aspect of the present disclosure comprises a radioconjugate of an antibody specific for CD38 and a radionuclide for use in the treatment of multiple myeloma and/or non-hodgkins lymphoma.

In embodiments, the radioconjugate comprises an antibody specific for CD38 comprising an HCDR1 region of sequence GFTFSSYYMN (SEQ ID NO: 1) or SYYMN (SEQ ID NO: 14), an HCDR2 region of sequence GISGDPSNTYYADSVKG (SEQ ID NO: 2), an HCDR3 of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and a radionuclide for the treatment of multiple myeloma and/or non-hodgkins lymphoma.

In certain embodiments, the radioconjugate comprises an isotope that exhibits a short range in tissue, e.g., a range of approximately 40-100 μm, combined with a high energy, e.g., approximately 4-9 MeV. In particular embodiments, such an isotope is an α-particle emitting isotope, for example, $^{213}$Bi or $^{225}$Ac.

In embodiments, the radioconjugate comprises a radionuclide selected from iodine-131, yttrium-90, lutetium-177, copper-67, astatine-211, bismuth-212, bismuth-213, and actinium-225.

In an embodiment, the radionuclide is bismuth-213.

In embodiments, the antibody specific for CD38 comprises an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and the radionuclide is bismuth-213.

In an aspect the radioconjugate is used for the treatment of multiple myeloma and/or non-hodgkins lymphoma.

An aspect relates to pharmaceutical compositions comprising the radioconjugate. In embodiments, the composition comprises an acceptable carrier. In embodiments, the composition is administered in an effective amount.

An aspect relates to a radioconjugate comprising an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and $^{213}$Bi for the treatment of multiple myeloma and/or non-hodgkins lymphoma.

In a further embodiment the antibody comprises a variable heavy chain of the sequence QVQLVESGGGLVQPGGSLRLSCAASGFTF SSYYMNWVRQAPGKGLEWVSGISGDPS NTYYADSVKGRFTISRDNSKNTLYLQM NSLRAEDTAVYYCARDLPLVYTGFAYWGQGTLVTVSS (SEQ ID NO: 10) and a variable light chain of the sequence DIELTQPPSVSVAPGQTARISCSGDNLRHYYVY WYQQKPGQAPVLVIYGDSKRPSGIPERFSGSN SGN-TATLTISGTQAEDEADYYCQTYTGGASLVFGGGT-KLTVLGQ (SEQ ID NO: 11).

In embodiments the antibody has an IgG1 Fc region. In embodiments the antibody comprises a modified Fc region, wherein said modification enhances ADCC activity.

In another aspect the radioconjugate of an antibody specific for CD38 comprising an HCDR1 region of sequence GFTFSSYYMN (SEQ ID NO: 1) or of sequence SYYMN (SEQ ID NO: 14), an HCDR2 region of sequence GIS-GDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and $^{213}$Bi is able to mediate killing of CD38-expressing OPM2 cells with an at least two-fold, three-fold, four-fold, or five-fold better efficacy than $^{213}$Bi alone.

In another aspect the radioconjugate of an antibody specific for CD38 comprising an HCDR1 region of sequence GFTFSSYYMN (SEQ ID NO: 1) or of sequence SYYMN (SEQ ID NO: 14), an HCDR2 region of sequence GIS-GDPSNTYYADSVKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and $^{213}$Bi inhibits tumor growth in a multiple myeloma mouse model.

Another aspect comprises a method of treating multiple myeloma and/or non-hodgkins lymphoma in an individual in need thereof, which method comprises administration of a radioconjugate comprising an antibody specific for CD38 comprising an HCDR1 region of sequence GFTFSSYYMN (SEQ ID NO: 1) or of sequence SYYMN (SEQ ID NO: 14), an HCDR2 region of sequence GISGDPSNTYYADSVKG (SEQ ID NO: 2), an HCDR3 region of sequence DLPLVYT-GFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and $^{213}$Bi to an individual having multiple myeloma or non-hodgkins lymphoma.

7. EXAMPLES

Example 1

CD38 Expression on the Surface of Various Cell Lines

The cell lines of Table 1 were tested for levels of CD38 expression.

TABLE 1

| Cell Line | Supplied by: | Cultivated in: |
| --- | --- | --- |
| AMO-1: Multiple Myeloma Cell Line | DSMZ #ACC 538 | RPMI1640, with L-Glutamine, (PAN Biotech GmbH, Cat No.: P04-16500 medium) |
| LP1: Multiple Myeloma Cell Line | DSMZ #ACC 41 | Iscove's Modified Dulbecco's Medium (IMDM) with GlutaMAX™ (Invitrogen, Cat No.: 31980-048) |

TABLE 1-continued

| Cell Line | Supplied by: | Cultivated in: |
| --- | --- | --- |
| NCI-H929: Multiple Myeloma Cell Line | DSMZ #ACC 163 | RPMI1640 (same as AMO-1), supplemented with 1 mM Na-Pyruvate, 50 µM β-Mercaptoethanol |
| RPMI8226: Multiple Myeloma Cell Line | DSMZ #ACC 402 | RPMI1640 (same as AMO-1) |
| OPM-2: Multiple Myeloma Cell Line | DSMZ #ACC 50 | RPMI1640 (same as AMO-1) |
| Plasmacytoma, Malignant Plasma Cells | Klinikum rechts der Isar | RPMI1640 (same as AMO-1) |

Bone marrow samples (4-10 ml aspirate) from multiple myeloma patients and extramedullary tumor plasmacytoma samples were obtained after informed consent from the Klinikum rechts der Isar ("KrdI") (Munich, Germany). Samples were subjected to centrifugation, and further plasma cell enrichment was achieved via magnetic-activated cell sorting.

Cells were stained with a directly labelled Quanti-BRITE™ CD38-PE antibody (Becton Dickinson GmbH, Clone HB7, CAT #342371), which is specific for CD38. The "Antibodies Bound Per Cell" (ABC's) were determined using the flow cytometry based QuantiBRITE™ system, which measures the geometric mean (GeoMean) per cell. Conversion of measured GeoMean into correlating ABC amount per cell was done with GraphPad PRISM™ software. The ABC values are assumed to correlate with the number of CD38 molecules per cell, since QuantiBRITE™ CD38-PE carries one PE molecule per antibody. The results are shown in Table 2.

TABLE 2

| Cell line | Absolute number of ABC (CD38 expression) |
| --- | --- |
| AMO-1 | 25,000 |
| LP-1 | 125,000 |
| NCI-H929 | 195,000 |
| RPMI-8226 | 670,000 |
| OPM-2 | 38,000 |
| Plasmacytoma | 30,000 |

Example 2

Binding of $^{213}$Bi-Anti-CD38-MAb Conjugate to MM Cell Lines

Myeloma cell lines OPM2, ARH77, RPMI8226, U266 and bone marrow mesenchymal stem cells (BM-MSC) (provided by T. Dechow, Technische Universität München) were cultured in RPMI 1640 medium (Biochrom, Berlin, Germany) supplemented with 10% fetal bovine serum, 100 U/ml penicillin, 100 µg/ml streptomycin and 1% L-glutamine (all from Biochrom). Human Umbilical Vein Endothelial Cells (HUVEC; PromoCell, Heidelberg, Germany) were kept in Endothelial Cell Growth Medium (PromoCell, Heidelberg, Germany). All cells were cultivated at 37° C. in a humidified atmosphere with 5% CO2.

Primary myeloma cells were isolated from the bone marrow of two patients suffering from multiple myeloma. The ficoll gradient solution Histopaque-1077 was covered with bone marrow and centrifuged at 445 g for 35 min (20° C.). From the interphase containing mononuclear cells, myeloma cells were isolated magnetically using anti-CD138 microbeads according to the instructions of the manufacturer (Miltenyi Biotec, Bergisch-Gladbach, Germany) Peripheral blood mononuclear cells (PBMC) were extracted from whole blood according to the protocol for extraction of primary myeloma cells.

$3\times10^5$ cells (in 200 µl culture medium) were seeded per well (coated with poly-D-lysine) of a 96-well plate and incubated for 1 h at 37° C. Subsequently cells were incubated with the anti-CD38-MAb MOR03087 (2 µg/ml) for another hour at 37° C. and washed three times with PBS/10% FCS on ice. Cells were then fixed for 10 min in 4% formaldehyde (in PBS) and permeabilized for 10 min with 1% Triton-X100 (in TBS). After washing (three times with PBS) and blocking for 1 h with PBS/10% FCS cells were incubated with a HRP-conjugated anti-human IgG antibody (1:5000 in TBS/10% FCS). Cells were washed three times with PBS and then incubated with Slow TMB substrate (Thermo Scientific Pierce, USA) for 1 h. The color reaction was stopped with 0.5 M H2SO4 and absorbance was measured at 450 nm.

The $^{213}$Bi chelating agent SCN-CHX-A"-diethylenetriaminepentaacetic acid (DTPA) (Macrocyclics, USA) was covalently coupled to anti-CD38-MAb as described previously in Mirzadeh et al., 1990, Bioconjug Chem. 1(1):59-65, which is incorporated by reference in its entirety. The α-emitter $^{213}$Bi was eluted from an $^{225}$Ac/$^{213}$Bi generator system provided by the Institute for Transuranium Elements (European Commission, JRC, Germany) (Apostolidis et al., 2005, AnalChem. 77:6288-6291; Morgenstern et al., 2012, Curr. Radiopharm. 5(3):221-227). Chelated anti-CD38-MAb (100 µg) was incubated with $^{213}$BiI4-/$^{213}$BiI52-anionic species, as eluted from the generator, for 7 min in 0.4 M ammonium acetate buffer at pH 5.3. Unbound $^{213}$Bi ions were separated from $^{213}$Bi-anti-CD38-MAb immunoconjugates by size-exclusion chromatography (PD-10 columns, GE Healthcare, Germany). Purity of $^{213}$Bi-anti-CD38 immunoconjugates was checked via instant thin-layer chromatography (Nikula et al 1995, Nucl. Med. Biol. 22:387-390). Binding of $^{213}$Bi-anti-CD38 immunoconjugates to OPM2 cells was analysed as described previously (Huber et al 2003, Clin. Cancer Res. 9(10Pt2):39225-39825). The $EC_{50}$ of the CHX-A"-DPTA-anti-CD38-MAb was 16.4 nM, indicating that the affinity of the conjugate is appropriate for therapeutic use.

The results are shown in FIG. 2A-2B. The percentage of bound $^{213}$Bi-labelled antibody was 11.8% in RPMI cells, 4.9% in OPM2 cells and 1.6% in ARH77 cells (FIG. 2A), indicating differential CD38 expression in the investigated cell lines. Likewise, $LD_{50}$ values for $^{213}$Bi-anti-CD38-MAb differed in the different cell lines: 0.185 MBq/ml for RPMI cells, 0.555 MbQ/ml for OPM2 cells, and 71.85 MBq/ml for ARH77 cells, as determined by CellTiter96® cell viability assay (FIG. 2B). For further analysis and experimental therapeutic studies, OPM2 cells were chosen for the intermediate binding results to better reflect the variance of CD38 expression in the clinical situation.

Example 3

Cell Death in MM Cells after Treatment with $^{213}$Bi-Anti-CD38-MAb Conjugate

Figure 3:
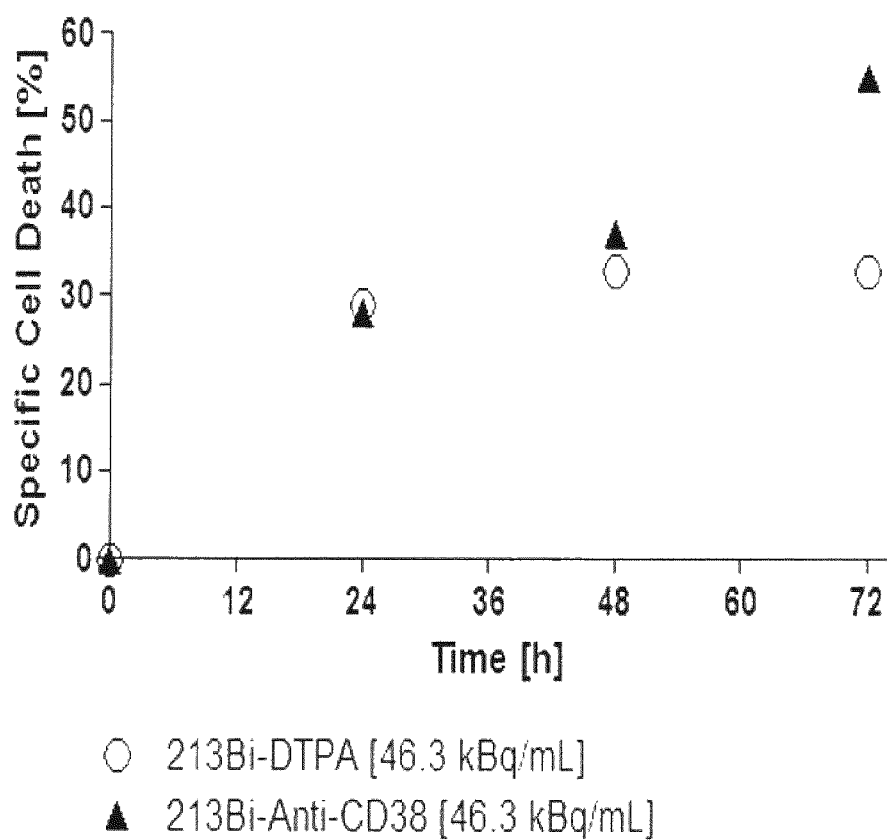
FIG. 3 shows the Quantification of Cell death after treatment of OPM2 cells with $^{213}$Bi-anti-CD38-MAb (Trypan Blue Assay).
Figure 4:
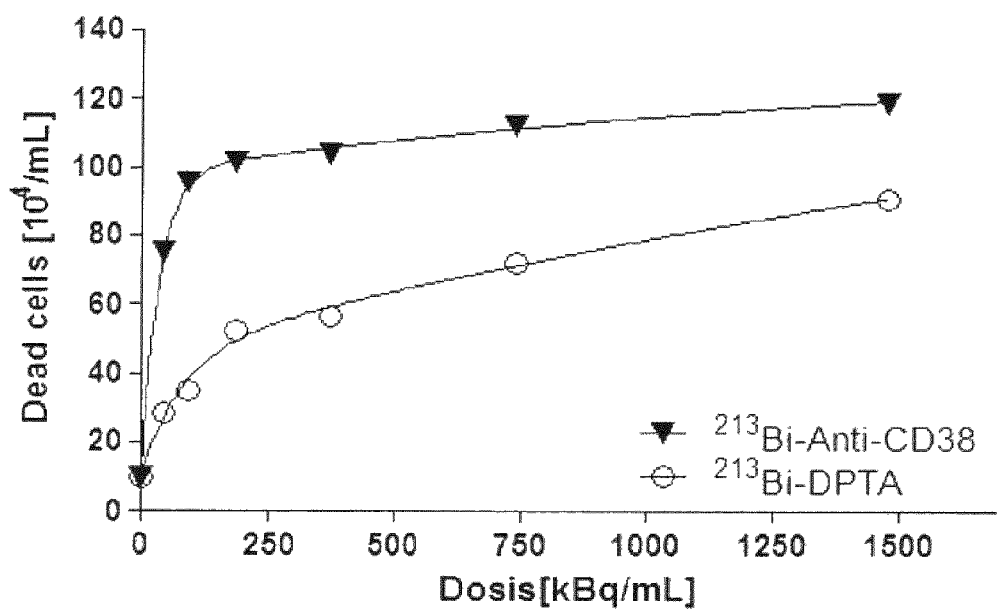
FIG. 4 shows the Quantification of Cell death after treatment of OPM2 cells with $^{213}$Bi-anti-CD38-MAb (Trypan Blue Assay).

For determination of the LD50 value OPM2 cells were seeded in 96-well plates ($1\times10^5$ per well in 100 µl culture medium) and incubated with different activity concentrations of $^{213}$Bi-DTPA or $^{213}$Bi-anti-CD38-MAb ranging from 46.3 kBq/ml to 1.48 MBq/ml for 1 h at 37° C. Cells were washed once with PBS in incubated in fresh medium for 96 h. Cells were then stained with trypan blue for detection of dead cells. The numbers of dead cells were counted microscopically. For determination of kinetics of cell death induction, OPM2 cells ($1\times10^5$ per well of a 96-well plate) were incubated with 46.3 kBq/ml of $^{213}$Bi-anti-CD38-MAb (corresponding to the LD50 value) for 1 h at 37° C. After washing once in PBS cells were incubated in fresh culture medium for another 24 h, 48 h, 72 h, 96 h or 120 h. Dead cells were then counted after trypan blue staining. The results are shown in FIGS. 3 and 4.

Figure 5:
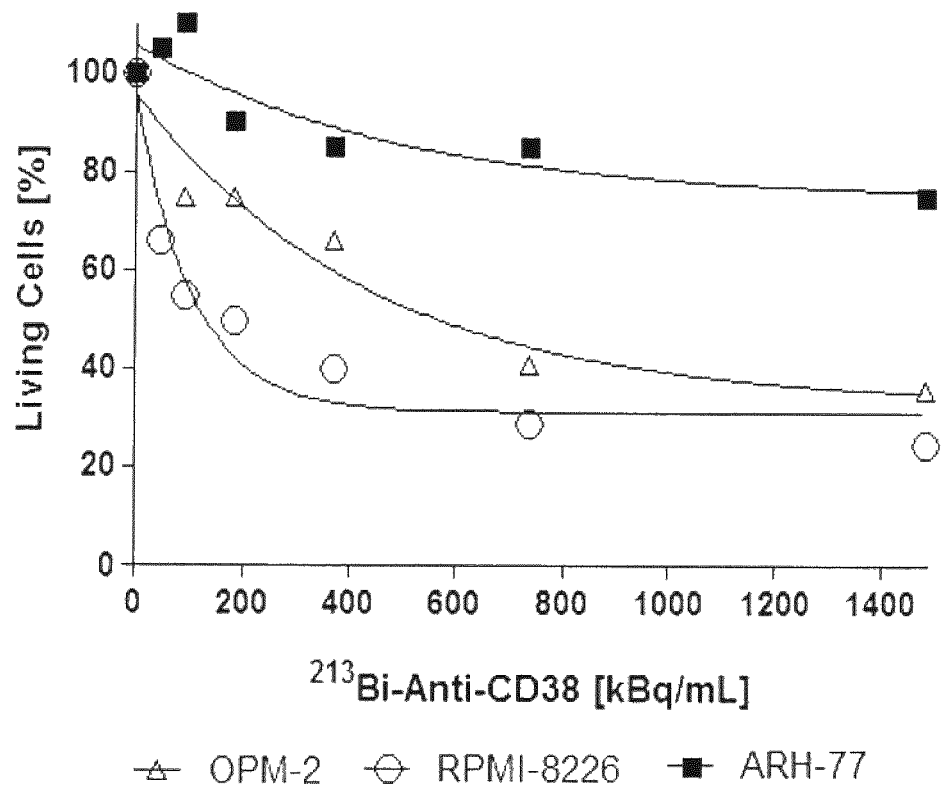
FIG. 5 shows the Quantification of Cell death after treatment of MM cells with $^{213}$Bi-anti-CD38-MAb (Trypan Blue Assay).

OPM2, RPMI and ARH77 cells ($2\times10^4$ in 100 µl culture medium per well) were seeded in 96-well plates and incubated with $^{213}$Bi-anti-EGFR-MAb activity concentrations ranging from 46.3 kBq/ml to 1.48 MBq/ml. At 48 h after initiation of treatment viability of cells was assayed in comparison to untreated cells using the CellTiter96® cell proliferation assay (Promega, Madison, USA). For that purpose 15 µl of dye solution was added to each well and the plates were incubated for 4 h at 37° C. in a humidified $CO_2$ incubator. Subsequently 100 µl of solubilisation/stop solution (formazan product) was added to each well and the absorbance was recorded one hour later at 570 nm using a 96-well plate reader (BioTek, Bad Friedrichshall, Germany) according to the manufacturer's instructions. The results are shown in FIG. 5.

Example 4

$^{213}$Bi-Anti-CD38-Induced DNA Double-Strand Breaks in OPM2 and ARH77 Cells

Induction of DNA double-strand breaks by treatment with $^{213}$Bi-anti-CD38-MAb (1.48 MBq/ml for 3 h at 4° C.) was tested on OPM2 and ARH77 cells and demonstrated to be different according to the different cell binding of $^{213}$Bi-anti-CD38 immunoconjugates.

In particular, OPM2 and ARH77 cells were seeded in 8-chamber slides covered with poly-L-lysin ($2.5\times10^4$ cells per chamber) and treated with $^{213}$Bi-anti-CD38-MAb (1.48 MBq/ml) for 3 h at 4° C. to prevent DNA-repair. Cells were washed with PBS and incubated in culture medium at 37° C. to allow DNA-repair. At various time points, γH2AX was detected by immunofluorescence. For that purpose, cells were fixed in 2% paraformaldehyde, washed with PBS and permeabilized with ice-cold methanol, washed with PBS and incubated with anti-γH2AX antibody (Millipore, Schwalbach/Ts, Germany; 1 h, RT) and anti-IgG antibody coupled with FITC (1 h, RT). Detection and quantification of immunofluorescence signals was done by image analysis using the Definiens Cognition Network Technology®.

At 0.5 h after treatment, numbers of γH2AX foci per cell reached a maximum for both cell lines, however in OPM2 cells number of γH2AX foci was approximately 2.5 fold higher compared to ARH77 cells. In OPM2 cells, the number of γH2AX foci decreased with time but did not reach control values even after 24 h. In contrast, in ARH77 cells, control values were already reached 2 h after incubation with $^{213}$Bi-anti-CD38-MAb (FIG. 6). Without wishing to be bound by any particular theory or mechanism, this could be due to the comparatively low number of induced γH2AX foci or to a better repair capacity of ARH77 cells compared to OPM2 cells.

Example 5

$^{213}$Bi-Anti-CD38-MAb Induces Mitotic Cell-Cycle Arrest and Subsequent Mitotic Catastrophe in OPM2 Cells Cell cycle arrest of OPM2 cells following treatment with $^{213}$Bi-anti-CD38-MAb (1.85 MBq/ml) for 3 h at 37° C.) was investigated by flow cytometry. In particular, OPM2 cells ($5\times10^6$ per 75 cm$^2$ culture flask) were incubated with or without $^{213}$Bi-anti-CD38 immunoconjugates (1.48 MBq/ml) for 3 h at 37° C. Subsequently cells were washed once with PBS and incubated in fresh culture medium for the indicated time periods. Cells were washed in PBS and fixed in 0.5 ml 80% ethanol. For cell-cycle analysis, fixed cells were incubated with RNase (0.1 mg/ml; 5 min RT), treated with pepsin (5 mg/ml in 50 mM HCl; 10 min 37° C.), stained with PI (50 µg/ml) and subjected to flow cytometric analysis (FACScalibur, Becton Dickinson).

The percentage of OPM2 cells arrested in G2 phase increased at 12 h, 18 h and 24 h after treatment and reached a maximum of 55% at 48 h. Concurrently, the percentage of OPM2 cells in G1 phase dropped below 15% at 48 h. In contrast, the level of untreated OPM2 cells (controls) in G2 and G1 phase remained constant at approximately 20% and 50%, respectively, throughout the observation period (FIG. 7A-7B). The results are illustrated using representative histograms showing the proportions of cells in G1, S and G2 phase in untreated and $^{213}$Bi-anti-CD38-MAb treated OPM2 cells (FIG. 7C).

To further characterize the cell cycle phase in which the cells are arrested, dual parameter flow cytometry with phospho-histone H3 staining was performed. In particular, OPM2 cells ($2\times10^6$ per well of a 6-well plate) were incubated with or without $^{213}$Bi-anti-CD38 immunoconjugates (0.74 MBq/ml). At 120 h after treatment cells were washed once with PBS and fixed in ice-cold 70% ethanol. Cells were washed again with PBS and incubated with anti-phospho-histone-H3 antibody (1:200; Cell Signaling Technology/New England Biolabs, Frankfurt, Germany) in 1% BSA for 3 h at room temperature (RT). After washing with PBS cells were incubated with the secondary anti-IgG antibody coupled with FITC (from rabbit, 1:1000; Abcam, Cambridge, UK) for 1 h at RT. Finally, cells were washed with PBS and resuspended in 5 µg/ml propidium iodide (PI)+RNase 0.1%. PI and FITC fluorescence of cells were analyzed by dual-parameter flow cytometry.

Figure 8A:
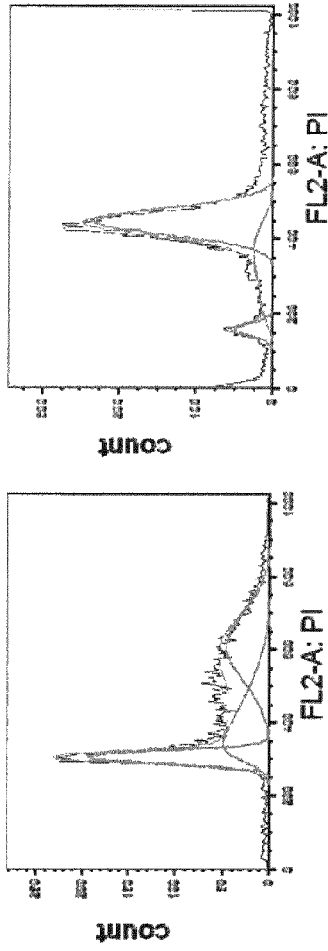
Figure 8B:
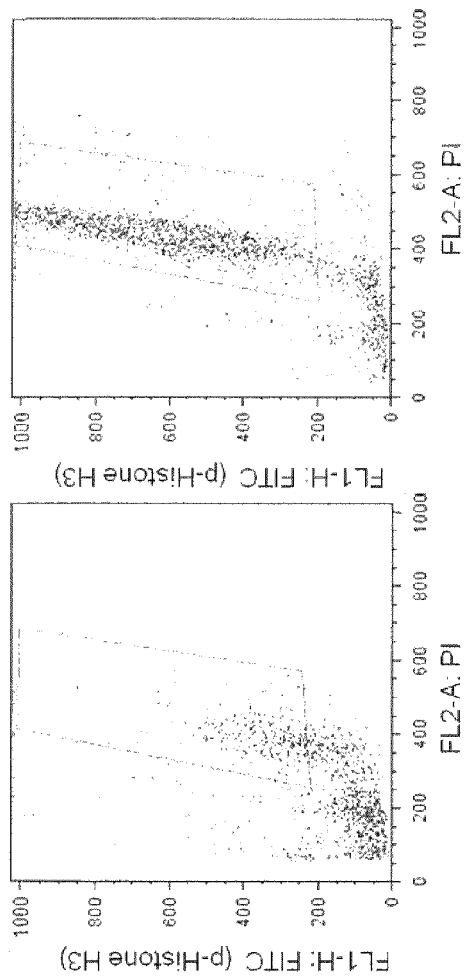
Figure 8D:
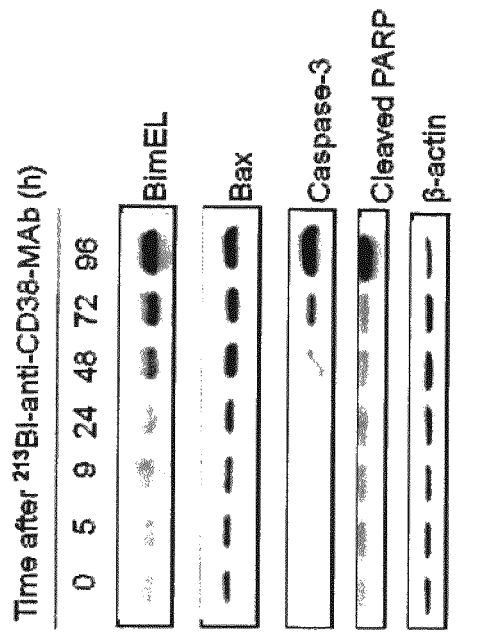
Figure 8C:
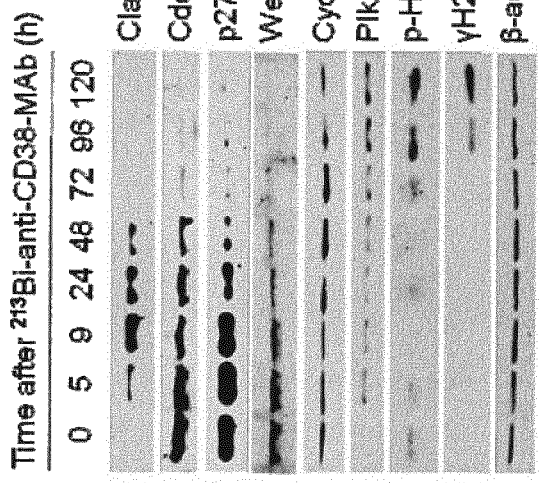

Histone H3 is phosphorylated at serine 10 upon entrance of cells into mitosis and phosphorylation correlates with mitotic chromosome condensation (Wei Y, et al., 1999, Cell 97(1):99-109). As shown in FIG. 8A, 120 h after treatment with $^{213}$Bi-anti-CD38-MAb (0.74 MBq/ml), OPM2 cells were arrested with a 4n DNA content, indicative of a G2/M arrest, and as shown in FIG. 8B, demonstrate a strong increase in histone H3 phosphorylation, indicating that cells had entered mitosis despite the treatment with DNA damaging α-irradiation Additional characterization was performed via immunoblotting of cell extracts. Major G2/M checkpoint activating events like claspin and Wee1 stabilisation, as well as Plk1 destabilization (Bassermann, F, et al., 2008, Cell 134(2): 256) were absent despite the presence of DNA damage, as evidenced by the phosphorylation of histone H2AX (γH2AX) (FIG. 8C). Instead, cells entered mitosis (shown by phosphorylation of histone H3) and underwent subsequent apoptosis as demonstrated by the cleavage of PARP and pro-caspase 3 (FIG. 8D). It is noted that substantial stabilization of pro-apoptotic BimEL (Bcl-2 interacting mediator of cell death, extra long form), was observed (FIG. 8D) which, without wishing to be bound by any particular theory or mechanism, is consistent with BimEL being involved in this mitotic cell death event.

The observations described herein indicate that $^{213}$Bi-anti-CD38-MAb treatment of OPM2 cells induced significant DNA damage, which however does not result in the activation of the G2 DNA-damage-response checkpoint, but instead resulted in mitotic arrest and subsequent mitotic catastrophe.

Immunoblotting was performed as follows: OPM2 cells ($2\times10^6$ per well of a 6-well plate) were incubated with $^{213}$Bi-anti-CD38-MAb (0.74 MBq/ml). At different time points after start of incubation, i.e. at 0, 5, 9, 24, 48, 72, 96 and 120 h, cells were washed in PBS and subsequently lysed (50 mM Tris, pH 7.5; 250 mM NaCl; 0.1% Triton X-100; 1 mM EDTA; 50 mM NaF+protease inhibitors) at 4° C. for 10 min. Lysates were centrifuged (13,500 rpm, 4° C., 10 min) and supernatants (containing 25 µg of protein each; BCA protein assay kit, Pierce, USA) were subjected to SDS-PAGE. Western blotting using different antibodies against clapsin (gift from Michele Pagano), cdc20 (Santa Cruz Biotechnology, Heidelberg, Germany), p27 (BD Biosciences, Heidelberg, Germany), Plk1 (Invitrogen/Life Technologies, Darmstadt, Germany), wee1, cyclin B1, p-HH3, BimEL, Bax, cleaved PARP (all from Cell Signaling Technology/New England Biolabs, Frankfurt, Germany), γH2AX, active caspase-3 (all from Millipore, Schwalbach/Ts, Germany), peroxidase-conjugated monoclonal anti-β-actin antibody (clone 8226, Abcam, Cambridge, UK) and peroxidase-conjugated anti-rabbit IgG antibody (GE Healthcare, Hatfield, UK) was performed as described previously (Vallon, M, et al., 2010, Exp Cell Res. 316(3):412-421).

Example 6

$^{213}$Bi-anti-CD38-MAb Conjugate in MM Xenograft Mouse Model

OPM2-Luc-GFP cells ($2.5\times10^7$ in 100 µl PBS) were inoculated intraperitoneally into 6-8 week-old SCID-mice (Charles River, Germany) Twenty-five days after cell inoculation fractionated treatment was started: tumor bearing animals (n=9) received six intraperitoneal applications of $^{213}$Bi-anti-CD38-MAb (1.85 MBq each in 100 µl PBS) every third or fourth day (see FIG. 9), according to a therapeutic scheme that has been successfully applied in previous studies (Drecoll et al., 2009, PLoS One 4(5):e5715; Essler et al., 2012, Eur J. Nucl Med Mol Imaging 39(4): 602-12; Vallon et al., 2012, Eur J. Nucl Med Mol Imaging 39(12):1886-97). Correspondingly, animals of the control group (n=9) were injected intraperitoneally six times with 100 µl PBS. Efficacy of therapy was controlled non-invasively in two mice each of the treatment group and the control group by bioluminescence imaging of tumor development 34, 47, and 59 days after tumor cell inoculation. Thus, bioluminescence imaging was performed two days after the third treatment (d 34) and five as well as 17 days after the sixth treatment (d 47, d 59). Imaging was done with anesthetized mice 10 min after intraperitoneal injection of 300 µl D-luciferin (50 mM in 0.9% NaCl) using a cooled CCD-camera (Hamamatsu, Germany). Symptom-free survival was monitored up to 200 days after inoculation of tumor cells.

In mice bearing OPM2 xenografts, treatment with $^{213}$Bi-anti-CD38-MAb prolonged survival was observed compared to treatment with unspecific $^{213}$Bi-DTPA or PBS. Median survival was 60 days in the PBS group, 55 days in the $^{213}$Bi-DTPA group and 100 days in the $^{213}$Bi-anti-CD38 group. Three animals of the group treated with $^{213}$Bi-anti-CD38-MAb survived longer than 200 days (FIG. 10). As demonstrated by non-invasive bioluminescence imaging in two animals, tumor size remained constant after treatment with $^{213}$Bi-anti-CD38-MAb at days 34, 47, and 59 after tumor cell inoculation, whereas it drastically increased in PBS treated mice (FIG. 11). Accordingly, the tumor weights were significantly different in $^{213}$Bi-anti-CD38-MAb and PBS treated mice (FIG. 12).

In an additional experiment, OPM2-Luc-GFP cells (2.5× $10^7$ in 100 µl PBS) are inoculated intraperitoneally into 6-8 week-old SCID-mice (Charles River, Germany) Twenty-five days after cell inoculation fractionated treatment is started: tumor bearing animals (n=9) received intraperitoneal applications of MOR202. Efficacy of therapy is controlled non-invasively in two mice each of the treatment group and the control group by bioluminescence imaging of tumor development 34, 47, and 59 days after tumor cell inoculation. Thus, bioluminescence imaging is performed two days after the third treatment (d 34) and five as well as 17 days after the sixth treatment (d 47, d 59). Imaging is done with anesthetized mice 10 min after intraperitoneal injection of 300 µl D-luciferin (50 mM in 0.9% NaCl) using a cooled CCD-camera (Hamamatsu, Germany) Symptom-free survival is monitored up to 200 days after inoculation of tumor cells.

At day 59 after tumor cell inoculation, i.e. 17 days after the sixth treatment, three mice of every group were sacrificed and the remaining tumor tissue as well as different organs (heart, liver, lung, spleen, pancreas, bone, brain, kidneys, stomach and intestine) were dissected, weighed and fixed in 4% buffered formalin. Subsequently, organs and tumors were embedded in paraffin. Slices of the major organs (4 µm) were stained with haematoxylin and eosin (H&E) and subjected to toxicity analysis. For detection and quantification of necrosis 1 µm thick paraffin slices were stained with H&E and evaluated with TissueMap image analysis software (Definiens, Munich, Germany). For immunohistochemical detection of apoptotic cells, paraffin slices were dewaxed, rehydrated and incubated with an anti-caspase-3 antibody (1:100; Abcam, Cambridge, UK) for 2 h at room temperature. Anti-caspase-3 antibody binding was verified using a secondary antibody labelled with horseradish peroxidase and DAB (3,3-diaminobenzidine tetrahydrochloride) as a substrate (DAB Detection Kit, Roche-Ventana, Penzberg, Germany) Immunohistochemical analysis was performed automatically using the CC1 program of the immunostainer Discovery XT device (Roche-Ventana, Penzberg, Germany). Images were acquired using a virtual microscope system (Olympus-Dotslide, version 2.0, Hamburg, Germany). Finally, quantification of the percentages of apoptotic cells present in the tumor sections was done using Definiens TissueMap software.

Immunohistochemical detection of apoptotic cells in remaining tumor tissue via active caspase-3 was performed two weeks after the last treatment cycle and showed high numbers of apoptotic cells in tumors from animals treated with $^{213}$Bi-anti-CD38-MAb but not in PBS controls (FIG. 13A). The same holds true for detection of necrotic cells in H&E stained tumor slices using TissueMap image analysis software (FIG. 13B). Furthermore, analysis of H&E stained slices of the major organs did not reveal any signs of toxicity.

What is claimed is:

1. A radioconjugate comprising an antibody specific for CD38 comprising an HCDR1 region of sequence GFTFSSYYMN (SEQ ID NO: 1) or SYYMN (SEQ ID NO: 14), an HCDR2 region of sequence GIS[ ]GDP[ ]SNTYY[ ]AD[ ]S[ ]VKG (SEQ ID NO: 2), an HCDR3 of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6).

2. The radioconjugate of claim 1, wherein the HCDR1 region comprises SYYMN (SEQ ID NO: 14).

3. The radioconjugate of claim 1, wherein the radionuclide comprises an alpha particle emitting isotope.

4. The radioconjugate according to claim 1, wherein the radionuclide is selected from iodine-131, yttrium-90, lutetium-177, copper-67, astatine-211, bismuth-212, bismuth-213, and actinium-225.

5. The radioconjugate according to claim 4, wherein the radionuclide is bismuth-213.

6. The radioconjugate according to claim 1, wherein the antibody comprises a variable heavy chain of the sequence QVQLVESGGGLVQPGGSLRLSCAASGFTF SSYYMNWVRQAPGKGLEWVSGISGDPSNT YYADSVKGRFTISRDNSKNTLYLQMNSLRAEDTAVYYCARDLPLVYTGFA YWGQGTLVTVSS (SEQ ID NO: 10) and
a variable light chain of the sequence DIELTQPPSVSVAPGQTARISCSGDNLRHYYWWYQQKPGQAPVLVIYGDSKRPSGIPERFS[ ]GSNSGNTATLTISGTQAEDEADYYCQTYTGGASLVFG GGTKLTVLGQ (SEQ ID NO: 11).

7. The radioconjugate according to claim 1, wherein the antibody comprises an IgG1 Fc region.

8. The radioconjugate according to claim 1, wherein the antibody comprises a modified Fc region, wherein said modification enhances ADCC or CDC activity.

9. A method of treating multiple myeloma in an individual in need thereof, comprising administration of a radioconjugate according to claim 1.

10. The method of claim 9, wherein the radioconjugate comprises an antibody specific for CD38 comprising an HCDR1 region of sequence GFTFSSYYMN (SEQ ID NO: 1) or of sequence SYYMN (SEQ ID NO: 14), an HCDR2 region of sequence GIS[ ]GDP[ ]SNTYY[ ]AD[ ]S[ ]VKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and 213Bi.

11. The method of claim 10, wherein the HCDR1 region of the radioconjugate comprises SYYMN (SEQ ID NO: 14).

12. The method of claim 10, wherein the radioconjugate comprises an antibody region that comprises a variable heavy chain of the sequence QVQLVESGGGLVQPGGSLRLSCAASGFTFSS YYMNWVRQAPGKGLEWVSGISGDPSNTYYADS VKGRFTISRDNSKNTLYLQMNSLRAEDTAVYYCARDLPLVYTGFAYWGQGTLVTVSS (SEQ ID NO: 10) and
a variable light chain of the sequence DIELTQPPSVSVAPGQTARISCSGDNLRHYYWWYQQKPGQAPVLVIYGDSKRPSGIPERFS[ ]GSNSGNTATLTISGTQAEDEADYYCQTYTGGASLVF GGGTKLTVLGQ (SEQ ID NO: 11).

13. A method of treating non-hodgkin's lymphoma in an individual in need thereof, comprising administration of a radioconjugate according to claim 1.

14. The method of claim 13, wherein the radioconjugate comprises an antibody specific for CD38 comprising an HCDR1 region of sequence GFTFSSYYMN (SEQ ID NO: 1) or of sequence SYYMN (SEQ ID NO: 14), an HCDR2 region of sequence GIS[ ]GDP[ ]SNTYY[ ]AD[ ]S[ ]VKG (SEQ ID NO: 2), an HCDR3 region of sequence DLPLVYTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and 213Bi.

15. The method of claim 14, wherein the HCDR1 region of the radioconjugate comprises SYYMN (SEQ ID NO: 14).

16. The method of claim 14, wherein the radioconjugate comprises an antibody specific for CD38 comprising an HCDR1 region of sequence GFTFSSYYMN (SEQ ID NO: 1) or of sequence SYYMN (SEQ ID NO: 14), an HCDR2 region of sequence GIS[ ]GDP[ ]SNTYY[ ]AD[ ]S[ ]VKG (SEQ ID NO: 2), an HCDR3 region of sequence DLPLWTGFAY (SEQ ID NO: 3), an LCDR1 region of sequence SGDNLRHYYVY (SEQ ID NO: 4), an LCDR2 region of sequence GDSKRPS (SEQ ID NO: 5), and an LCDR3 region of sequence QTYTGGASL (SEQ ID NO: 6) and 213Bi.

* * * * *